(12) United States Patent
Park et al.

(10) Patent No.: US 6,759,532 B2
(45) Date of Patent: Jul. 6, 2004

(54) METHOD FOR OBTAINING DNA FROM FISH SPERMATOGONIUM

(75) Inventors: Han Oh Park, Choongcheongbuk-Do (KR); In Woo Lee, Choongcheongbuk-Do (KR)

(73) Assignee: Bioneer Corporation (KR)

( * ) Notice: Subject to any disclaimer, the term of this patent is extended or adjusted under 35 U.S.C. 154(b) by 0 days.

(21) Appl. No.: 10/029,281

(22) Filed: Dec. 28, 2001

(65) Prior Publication Data

US 2002/0082416 A1 Jun. 27, 2002

Related U.S. Application Data

(63) Continuation of application No. 09/693,862, filed on Oct. 23, 2000.

(30) Foreign Application Priority Data

Oct. 23, 1999 (KR) .................................. 10-1999-0046220

(51) Int. Cl.$^7$ ............................. C07H 21/00; C12N 5/02
(52) U.S. Cl. ..................................... 536/25.41; 435/325
(58) Field of Search ............................. 536/25.4, 25.41, 536/24.2; 435/325, 189.6; 532/23.2, 23.5

(56) References Cited

U.S. PATENT DOCUMENTS

| 3,838,148 A | 9/1974 | Christen et al. |
| 5,625,053 A | 4/1997 | Kresheck et al. |

FOREIGN PATENT DOCUMENTS

| KR | 9 004219 | 6/1990 |

OTHER PUBLICATIONS

Accession No. 97:48249 CABA, 1996.*

Walsh et al., "Isolation Characterzation, and Synthesis of DNA from a Malaria Parasite", J. Rorozool., 1968, pp. 503–508, vol. 15, No. 3.

B.T. Pentecost et al., "Isolation and Sequence of CDNA Clones Coding for a Member of the Family of High Mobility Group Proteins (HMG–T) in trout and Analysis of HMG–T–mRNA's in Trout Tissues", Nucleic Acids, Research, 1985, vol. 13, No. 13, IRL Press Limited, Oxford England.

Puig et al., "Interaction Between N–Terminal Domain of H4 and DNA is Regulated by the Acetylation Degree" Biochimica et Biophysicia Acta 1397, 1998, pp. 79–90, Elsevier Science B.V.

R. Lundbland et al., "Chemical Reagents for Protein Modification ", 1984, pp. 137–170, vol. 1, CRC Press, Inc., Boca Raton, Florida.

J.F. Riordan et al., "Modification Reactions" Acetylation, Meth, Enzymol., 1967, vol. 11, pp. 565–570.

* cited by examiner

Primary Examiner—Anne-Marie Falk
Assistant Examiner—Celine Qian
(74) Attorney, Agent, or Firm—Nath & Associates PLLC; Todd L. Juneau; Lee C. Heiman

(57) ABSTRACT

A method for obtaining DNA from fish spermatogonia comprises (i) disrupting fish spermatogonium to obtain a milky-white colloid, (ii) adding an alkaline solution of pH 8 to pH 12, containing more than 1 mol of salts, such as monovalent salts, to the milky-white colloid, to separate DNA from protamines, and then (iii) adding ethanol solution to the resultant mixture, effecting a precipitation of DNA.

10 Claims, 3 Drawing Sheets

METHOD FOR OBTAINING DNA FROM FISH SPERMATOGONIUM

TECHNICAL FIELD OF THE INVENTION

The present invention relates to obtaining deoxyribonucleic acid (DNA) from fish spermatogonium in a large scale and, more particularly, to a methodology that entails disrupting fish spermatogonia, followed by a protein separation step and a DNA precipitation step.

BACKGROUND OF THE INVENTION

DNA is a biopolymer that encodes genetic information and that exists widely in various live organisms. DNA is composed of phosphorous acid, four (4) kinds of bases, deoxyribose, and has been widely used in biochemical experimental materials, cosmetics, medicines, food additives, and etc., due to its intrinsic physicochemical or biological properties.

Squid spermatogonium is a by-product obtained in a large amount from squid food processing industry. After it is captured and its intestines are eliminated, the squid is processed for producing dried squids or dried squid slices. The egg and spermatogonia of squid are processed for use of side dishes in restaurants. The spermatogonium of squid contains a larger amount of DNA than any other materials do and thus, can be used as a good DNA source. Traditionally, DNA has been obtained from spermatogonia of herring or salmon. Korean Patent No. 35973 discloses the use of an anionic surfactant and sodium chloride for producing DNA.

A process also has been disclosed for obtaining DNA in a large scale, either using phenol (U.S. Pat. No. 3,838,148) or using an anionic surfactant with a highly concentrated sodium chloride (Korean Patent No. 35973). However, these methods generate a large amount of pollutants during the process and thus, result in a high cost for treating the pollutants. Therefore, a new process for obtaining DNA from fish spermatogonium without generating of pollutants, preferably by-products produced from the process may be used for manure, has been desired in this field.

Therefore, the present inventors have studied for a long time to develop a novel and economic process for obtaining DNA from fish spermatogonium without the disadvantages of the prior methods, and have found that DNA can be obtained from fish spermatogonia effectively and economically, by using highly concentrated alkaline solution.

SUMMARY OF THE INVENTION

It therefore is an object of the present invention to provide a method for obtaining DNA from fish spermatogonia, avoiding the environmental and other problems of conventional techniques, by using highly concentrated alkaline solution without resort to a phenol which is harmful to humans, SDS (Sodium Dodecyl Sulphate), to an anionic surface active agent or an environmental pollutant, such as sodium chloride, which is harmful to soil. As a result, by-products generated during a DNA obtaining process of the present invention are suitable for use as plant nutrient.

Another object of the present invention is to provide a liquid nitrogenous manure containing by-products generated from the method of the present invention.

These and other objects of the present invention can be achieved via a method for obtaining DNA from fish spermatogonium that comprises:

i) disrupting a fish spermatogonium to produce a milky-white colloid containing DNA;

ii) treating the milky-white colloid with alkaline solution of pH 8 to pH 12 which contains more than 1 M of salts, such as a monovalent salt, to separate DNA from nucleosome; and iii) precipitating DNA by adding ethanol to the mixture obtained in the step (ii).

The above objects of the present invention are also achieved by providing a method for obtaining DNA from fish spermatogonium, which comprises:

i) disrupting a fish spermatogonium in an alkaline solution of pH 8 to pH 12 which contains more than 1 M of salts, such as monovalent salts;

ii) adding an anhydrous compound to the disrupted spermatogonium mixture obtained in the step (i), to effect acylation reaction;

iii) precipitating DNA by adding ethanol to the acylated spermatogonium mixture.

BRIEF DESCRIPTION OF THE DRAWINGS

The above objects and other advantages of the present invention will become more apparent by describing in detail a preferred embodiment thereof with reference to the attached drawings, in which.

DETAILED DESCRIPTION OF THE INVENTION

Figure 1:
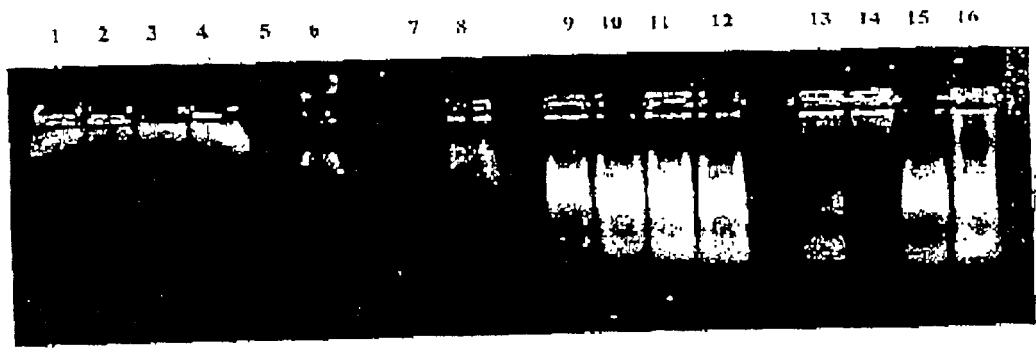
FIG. 1 is a photograph of agarose gel electrophoresis of DNA after treatment using the solution 1 and the solution 2, respectively, according to Example 1.

Spermatogonia of various kinds of fish can be used in the present invention. Preferably, the spermatogonia of squid or pollack, which are available abundantly and cheaply, may be used in the present invention.

Fish spermatogonium is disrupted by crusher in distilled water to produce colloid mixture. The colloid mixture is filtered through sieve to eliminate tissues which were not crushed, and then an alkaline solution with high salt concentration is added thereto. Also, fish spermatogonia may be disrupted in an alkaline solution with high salt concentration, or may be disrupted in distilled water followed by adding high salt concentration solution, and an alkaline solution of pH 8 to pH 12 is added thereto, sequentially. High salt concentration solution is understood to have more than 1 M of salts, more preferably not less than 4 M of salts.

The method of the present invention may further comprise a step for acylation reaction, wherein an anhydrous compound is added to the disrupted spermatogonium mixture which has been treated with alkaline solution. The anhydrous compound which can be used in the present invention include, but are not limited to, acetic anhydride, propyl anhydride or butyric anhydride. The alkaline compound which can be used in the present invention include, but are not limited to, sodium nitrate, sodium carbonate or sodium phosphate.

The method of the present invention may further comprises a step for RNA lysis by means of ribonuclease (RNase) or alkaline treatment, following disrupting the fish spermatogonium in the step (i).

Hereinafter, the methods of the present invention will be described in more detail. Upon disruption of cells, highly concentrated salts impart a strong positive charge to DNA binding proteins, which enables DNA binding proteins to be readily separated from DNA. DNA binding proteins such as protamines have a high content of lysine. Lysine contains an amine group that can be positively charged by highly concentrated salts. Amine groups with a positive charge in DNA binding proteins, can be deprotonized by alkaline solution to form highly reactive functional groups, which can react with anhydride resulting in loosing ionic affinity toward DNA (Roger L. Lundbland and Claudia M. Noyes., chemical Reagents for Protein Modification, Vol I CRC Press, Inc., 1984, page 130–131; Riordan, J. F. and Vallee, B. L., Acetylation, Meth. Enzymol., 11, page 565–570, 1967). Moreover, alkaline solution of the present invention is able to cause lysis of RNA. Therefore, DNA can be obtained without using RNase using the method of the present invention.

Upon reacting of the deprotonized amine group with anhydride, the amine groups of the protein and of RNA are acylated loosing a positive charge and then, the protein is not combined again with DNA under a low concentration of alkaline salts. Then, DNA is precipitated in fibrous form from the reaction mixture by addition of ethanol thereto. The DNA thus obtained is washed with ethanol and dried to produce a white DNA fiber. In order to make manure from the by-product of the above process, nitric acid or phosphoric acid equivalent to the base used in the process of the present invention, is added to the by-product mixture and then distilled simply after adjusting pH of said mixture to neutral.

The ethanol recovered from the distillation may be used again in the method of the present invention. The residual product after the distillation contains more than 90% of nitrate, various organic materials, phosphate salt, etc., and thus, may be used as manure without further processing. Sodium nitrate of which N2 content is 16%, is known as a soil reforming agent which converts the nature of soil into weak basic property. As given above, the method of the present invention can produce DNA without generating of pollutants which cause environmental problems, and also generates by-products which can be used for nitrogenous liquid manure. Accordingly, the method of the present invention has remarkable advantages over the prior methods, and specifically, is a more economic than conventional methods. The DNA obtained from the method of the present invention can be effectively separated as depicted in FIG. 1 to FIG. 4. It was confirmed that the DNA obtained from the present invention are pure through agarose gel electrophoresis after being treated with ribonuclease (RNase A) and deoxyribonuclease (DNase I).

The present invention is illustrated in greater detail with reference to the following examples. The examples are given for illustration of the invention and are not intended to limit the scope of the present invention.

EXAMPLE 1

25 g of squid spermatogonium were added into 300 ml of the solution containing 4 M $NaNO_3$, 0.1 M $Na_2CO_3$ and 20 mM EDTA (Solution 1, pH 11) and 300 ml of solution containing 4 M $NaNO_3$, 0.1 M $NaHCO_3$ and 20 mM EDTA (Solution 2, pH 8.3), respectively. The resulting solutions were ground with conventional mixer for 5 minutes and crushed with sonicator for 1 hour at 4° C. and then filtered. 2 ml of acetic anhydride was added into each filtrate thus obtained. The acylation reaction was effected at 4° C. for 1 hour. In order to remove protein selectively, ammonium sulfate was added to each filtrates until the final concentration of ammonium sulfate reaches 50% v/v, for precipitation reaction, before or after addition of acetic anhydride. Then, ethanol was added to each mixture until the final concentrations of ethanol reach 20% to 80% v/v, while stirring at 4° C. for 30 minutes, to precipitate DNA. DNA was collected from each mixtures by centrifugation, washed twice with 5 ml of 70% ethanol solution (water:ethanol 30:70 v/v), and then dried in air. The DNA thus obtained was dissolved in TE (Tris-EDTA) buffer, and was separated using a 1.8% agarose electrophoresis.

1.9 ml of distilled water was added on 0.1 ml of DNA TE buffer thus obtained. The optical densities of the DNA solutions thus prepared, were measured. The results thereof are represented in FIG. 1 and Table 1.

In FIG. 1, Lane 1 represents the electrophoresis result of the spermatogonium DNA obtained from the solution 1; Lane 2 represents the electrophoresis result of the spermatogonium DNA obtained from the solution 2; Lane 3 represents the electrophoresis result of the spermatogonium DNA obtained from the solution 1 followed by the treatment with acetic anhydride; Lane 4 represents the electrophoresis result of the spermatogonium DNA obtained from the solution 2 followed by the treatment with acetic anhydride; Lane 5 represents the electrophoresis result of the DNA prepared by ethanol precipitation of the supernatant separated from the protein precipitation process by means of ammonium sulfate, of spermatogonium DNA mixture obtained from the solution 1; Lane 6 represents the electrophoresis result of the DNA prepared through the same process as that of Lane 5 from solution 2; Lane 7 represents the electrophoresis result of the DNA prepared by ethanol precipitation of the supernatant separated from the protein precipitation process by means of ammonium sulfate, of spermatogonium DNA mixture acylated by acetic anhydride and obtained from solution 1; Lane 8 represents the electrophoresis result of the DNA prepared the same process as that of Lane 7 from solution 2; Lane 9 represents the electrophoresis result of the DNA prepared by precipitation with 20% v/v ethanol solution of the spermatogonium mixture acylated with acetic anhydride and obtained from the solution 1; Lane 10 represents the electrophoresis result of the DNA prepared through the same process as that of Lane 9 except for using t 40% ethanol solution; Lane 11 represents the electrophoresis result of the DNA prepared through the same process as that of Lane 9 except for using 60% v/v ethanol solution; Lane 12 and Lane 15 represent the electrophoresis result of the DNA prepared through the same process as that of Lane 9 except for using 80% v/v ethanol solution; Lane 13 represents the electrophoresis result of the DNA prepared by precipitation with ethanol solution of the spermatogonium mixture obtained from the solution 1 without acylation; Lane 14 represents the electrophoresis result of the DNA prepared through the same process as that of Lane 13 from solution 2; Lane 16 represents the electrophoresis result of the DNA prepared process same as that of Lane 15 from solution 2.

TABLE 1

The optical density of DNA prepared in Example 1

| | Solution: 4M NaNO₃, 0.1M Na₂CO₃, 20 mM EDTA | | | | Solution: 4M NaNO₃, 0.1M NaHCO₃, 20 mM EDTA | | | |
|---|---|---|---|---|---|---|---|---|
| | EtOH 20% | EtOH 40% | EtOH 60% | EtOH 80% | EtOH 20% | EtOH 40% | EtOH 60% | EtOH 80% |
| OD260 nm | 0.0578 | 0.1716 | 0.0888 | 0.2434 | 0.3195 | 0.6353 | 0.3408 | 0.3300 |
| OD280 nm | 0.0276 | 0.0824 | 0.0424 | 0.1589 | 0.2888 | 0.4175 | 0.2096 | 0.1820 |
| OD260/ OD280 | 2.09 | 2.08 | 2.09 | 1.53 | 1.11 | 1.52 | 1.63 | 1.81 |
| supernatant | Clear | clear | clear | clear | turbid | Turbid | turbid | Turbid |
| pellet | No | No | No | Small | Small | Small | Small | Small |

As illustrated in FIG. 1, DNA was obtained more efficiently by using acetic anhydride. The isolation efficiency of DNA using strong alkaline solution 1 (pH 11) was higher than that of DNA using weak alkaline solution 2 (pH 8.3). There was no significant difference in isolation efficiency depending on using of ammonium sulfate for the precipitation of protein. The optical density data in Table 1 represent that the purity of DNA obtained from strong alkaline solution 1 (pH 11) was higher than that of DNA obtained from weak alkaline solution 2 (pH 8.3).

EXAMPLE 2

51 g of squid spermatogonium were added into 500 ml of the solution containing 4 M NaNO3 and 0.1 M Na2CO3 (Solution 1, pH 11) and 500 ml of the solution containing 4 M NaNO3 and 0.1 M NaHCO3 (Solution 2, about pH 8.3), respectively. The resulting solutions were ground with conventional mixer for 5 minutes and crushed with sonicator for 1 hour at 4° C. and then filtered. 2 ml of acetic anhydride was added to each filtrate thus obtained. The acylation reaction was effected for 1 hour at 4° C. Then, 2 ml of acetic anhydride was added again to each reaction mixture. The reaction mixtures were crushed with sonicator for 15 minutes. The acylation reaction was effected at 4° C. for 1 hour again. Then, ethanol was added to each mixture until the final concentrations of ethanol reach 20%, 40%, 60%, 80% (v/v), while stirring at 4° C. for 30 minutes, and until the final volume of mixtures reach 20 ml, to precipitate DNA. DNA thus precipitated was collected from each mixture through centrifugation washed twice with 5 ml of 70% ethanol solution, and then dried in vacuum to produce purified DNA. The DNA thus obtained was dissolved in TE (Tris-EDTA) buffer, and was separated using a 1.8% agarose electrophoresis.

Figure 2:
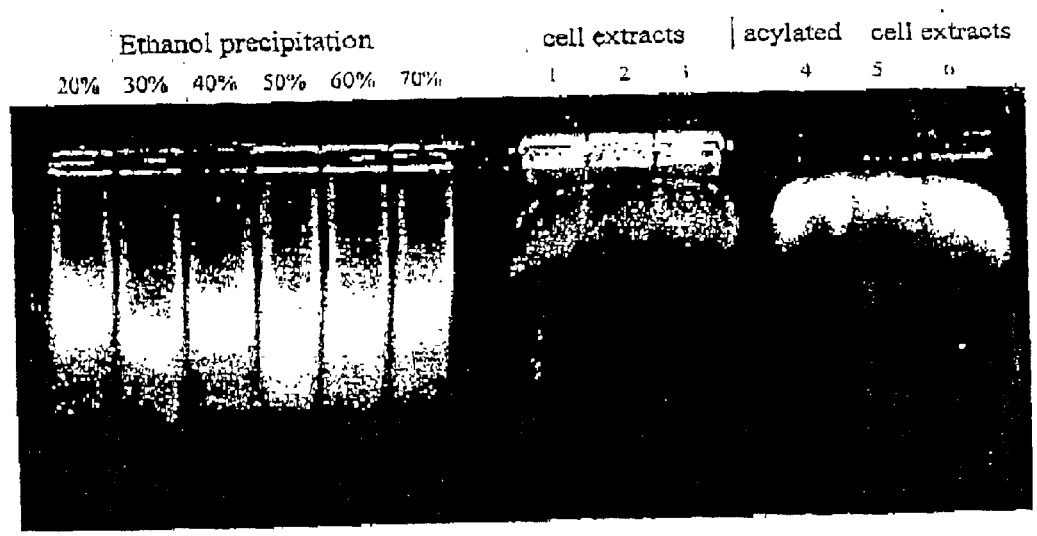
FIG. 2 is a photograph of agarose gel electrophoresis of DNA after treatment using different concentration of ethanol according to Example 2.

1.9 ml of distilled water was added to 0.1 ml of DNA TE buffer thus obtained. The optical densities of the DNA solutions thus prepared, were measured. The results thereof are represented in FIG. 2 and Table 3.

TABLE 2

The amounts of DNA with the change of concentration of ethanol

| | EtOH concentration | | | | | |
|---|---|---|---|---|---|---|
| | 20% | 30% | 40% | 50% | 60% | 70% |
| EtOH amount | 4 ml | 6 ml | 8 ml | 10 ml | 12 ml | 14 ml |
| DNA amount obtained | 16 ml | 14 ml | 12 ml | 10 ml | 8 ml | 6 ml |

In FIG. 2, Lane 1 and Lane 4 represents the result of electrophoresis of the DNA obtained from solution 1; Lane 2 and Lane 5 represents the result of electrophoresis of the DNA obtained from solution 2; Lane 3 and Lane 6 represents the result of electrophoresis of the DNA obtained from solution 1 without 20 mM EDTA which inhibits DNase activity.

TABLE 3

Optical Density measured with different concentrations of ethanol

| | 4M NaNO₃, 0.1M Na₂CO₃ | | | | | |
|---|---|---|---|---|---|---|
| | EtOH 20% | EtOH 30% | EtOH 40% | EtOH 50% | EtOH 60% | EtOH 70% |
| OD 260 nm | 0.4988 | 0.7562 | 0.4234 | 1.5054 | 1.1180 | 0.9714 |
| OD 280 nm | 0.2396 | 0.3650 | 0.2041 | 1.0277 | 0.7676 | 0.6759 |
| OD 260/ OD 280 | 2.08 | 2.07 | 2.08 | 1.47 | 1.46 | 1.44 |
| State of pellet in TE | clear | clear | clear | Turbid | turbid | turbid |
| Pellet not dissolved in TE | small | small | small | Small | small | small |

As illustrated in FIG. 2 and Table 3, yield was low, while purity was high when the concentration of ethanol was 20%, 30%, and 40%, and yield was high, while purity was low relatively when the concentration of ethanol was 40%, 50%, 60% and 70%. Furthermore, on a direct electrophoresis of cell extracts (lane 1-3), DNA became tangled with a protein component and remained as it is on the well, and DNA was separated efficiently from a protein component when acylation reaction was performed.

EXAMPLE 3

Figure 3:
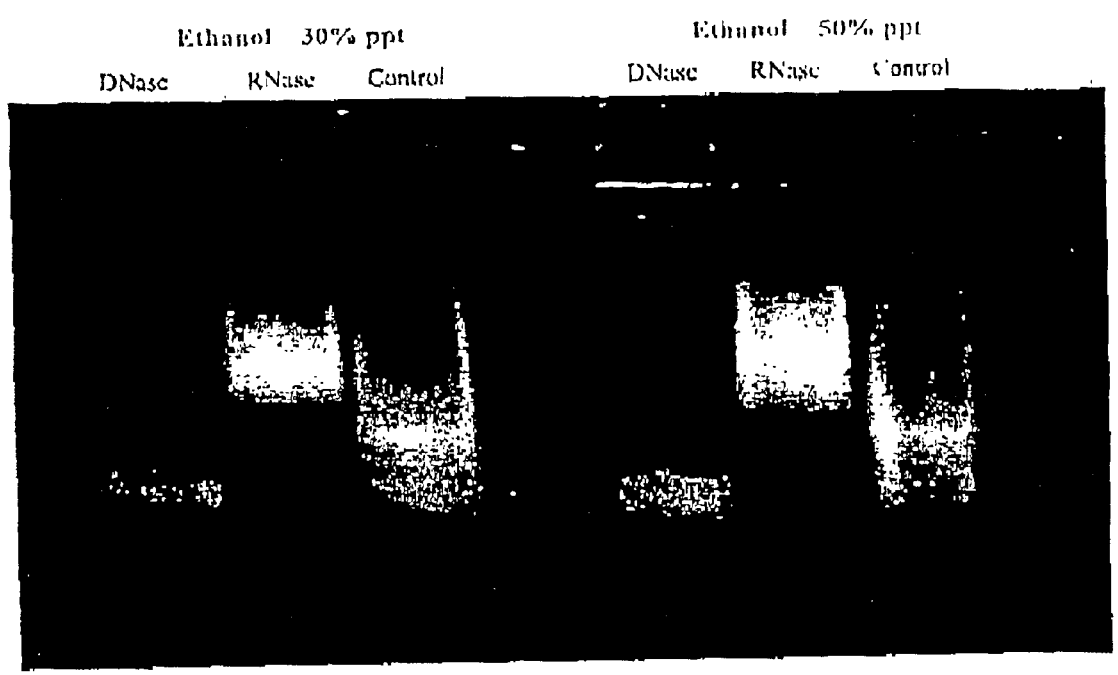
FIG. 3 is a photograph of agarose gel electrophoresis of DNA after treatment using DNase and RNase A according to Example 3.

To confirm whether purified DNA was obtained and separated in the Examples 1 and 2, the DNA obtained was treated with DNase and RNase. 10 μl of DNA sample obtained from the Examples 1 and 2, ten-fold concentrated reaction buffer (10 μl of 10 mM Tris, pH 7.6, 10 mM MgCl2, 50 mM NaCl, 1 mM Dithiothreitol (DTT), 10 μl of enzyme (DNase or RNase), 70 μl of D.W. were mixed until total volume are 100 μl The reaction was carried out at 36.7° C. for 2.5 hours, and then 1.8% agarose gel electrophoresis was performed after incubation at 4° C. overnight. The result was illustrated in FIG. 3. As illustrated in FIG. 3, DNA band still remained when using DNase, but DNA band did not remained when using RNase.

EXAMPLE 4

25 g of pollack spermatogonium were added into 300 ml of the solution containing 4 M NaNO₃ and 0.1 M Na₂CO₃ (Solution 1, pH 11). The resulting solution was ground with conventional mixer for 5 minutes, crushed with sonicator for 1 hour at 4° C. and then filtered. 2 ml of acetic anhydride was added into each filtrate thus obtained. The acylation reaction was effected for 1 hour at 4° C. Then 2 ml of acetic anhydride was added again to each reaction mixture. The acylation reaction was effected at 4° C. for 2 hours. Then, ethanol was added to each mixture until the final concentrations reach 50 to 60% v/v, while stirring at 4° C. for 30 minutes, to precipitate DNA. DNA was collected from each mixture through centrifugation, washed twice with 5 ml of 70% ethanol solution, and then dried in air. The DNA thus obtained was dissolved in TE(Tris-EDTA) buffer.

To confirm whether purified DNA was obtained and separated, the DNA obtained was treated with DNase. 10 μl of the DNA sample and ten-fold concentrated reaction buffer (10 μl of 10 mM Tris, pH 7.6, 10 mM MgCl2, 50 mM NaCl, 1 mM Dithiothreitol (DTT), 10 μl of enzyme (DNase) and 70 μl of D.W. were mixed until total volume was 100 μl. The reaction was carried out at 36.7° C. for overnight and then 1.8% agarose gel electrophoresis was performed.

Figure 4:
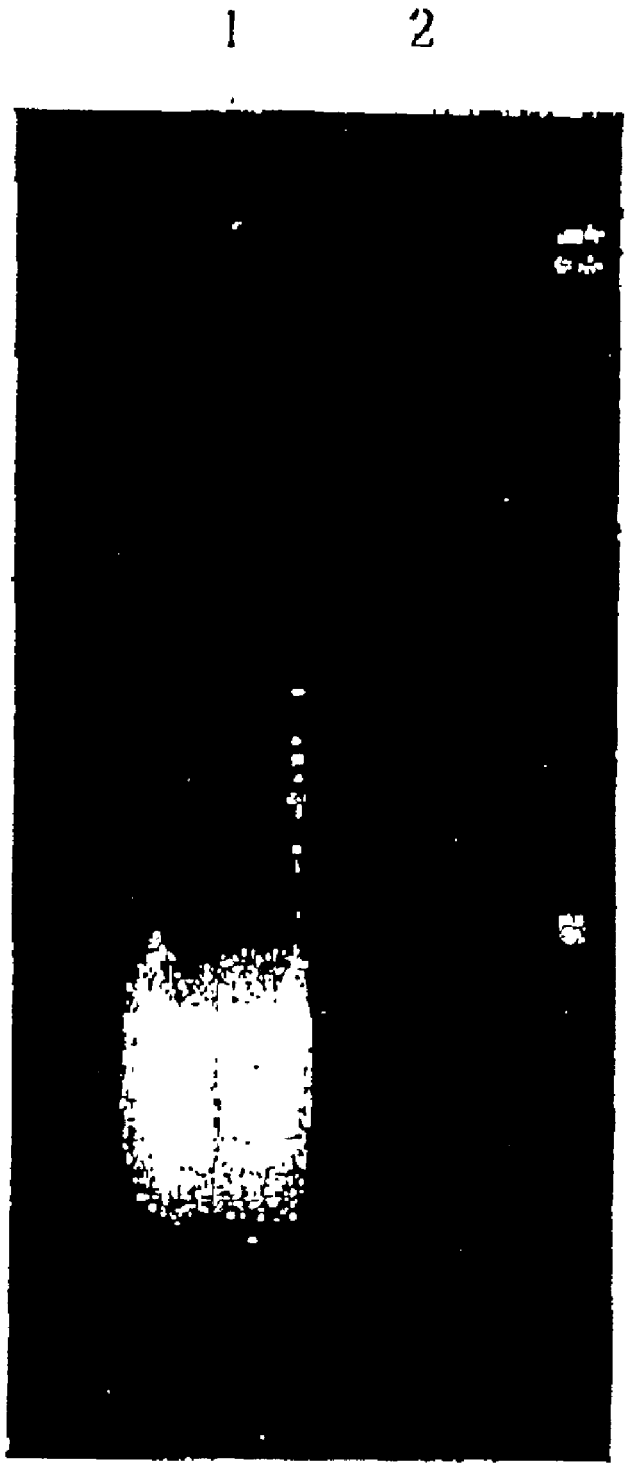
FIG. 4 is a photograph of agarose gel electrophoresis of DNA obtained from the pollack spermatogonium according to Example 4.

This result is illustrated in FIG. 4. As shown there, the DNA band did not remain when Dnase was employed. In FIG. 4, Lane 1 represents the result of electrophoresis of DNA obtained from spermatogonium of pollack; Lane 2 represents the result of electrophoresis of spermatogonium of pollack DNA after treating DNase. Moreover, upon measuring the Optical Density, OD260/280 is 1.93, and a concentration of DNA(mg/ml) is 1.15 in case acylation reaction was proceeded at room temperature, and OD260/280 is 1.96, and a concentration of DNA(mg/ml) is 1.05 in case acylation reaction was proceeded at low temperature. Therefore, obtaining efficiency was higher in low temperature acylation reaction than in high temperature acylation reaction.

As mentioned above, fish DNA can be separated easily and efficiently, pursuant to the present invention, without generating pollutants. Furthermore, the by-products of the present invention contains nitrate salt, phosphate salt, various organic material, etc. Accordingly, it is very economical to utilize the by-product as a component of liquid manure directly.

While the present invention has been particularly shown and described with reference to particular embodiments thereof, it will be understood by those skilled in the art that various changes in form and details may be effected therein without departing from the spirit and scope of the invention as defined by the appended claims.

This application claims priority from the Korean Patent Application No. 10-1999-0046220, the contents of which are hereby incorporated by reference in their entirety, including the specification, drawings and claims.

What is claimed is:

1. A process for obtaining deoxyribonucleic acid (DNA) from fish spermatogoflium, which comprises:
    i) disrupting a fish spermatogofliulfl to produce a milky-white colloid containing DNA;
    ii) adding an alkaline solution of pH 8 to pH 12 that contains not less than 4 M of salts selected from the group consisting essentially of sodium nitrite, sodium carbonite, and sodium phosphate to said milky-white colloid;
    iii) effectuating acylation reaction of a mixture obtained in step ii); and
    iv) adding ethanol solution to a mixture obtained iii step iii) to precipitate DNA.

2. The process according to claim 1, wherein said fish spermatogonium is selected from the group consisting of the spermatogonium of squid and the spermatogonium of pollack.

3. The process according to claim wherein said acylation reaction is performed by using anhydride compounds.

4. The process according to claim 1, wherein said anhydride compound is acetic anhydride.

5. The process according to claim 1, wherein said spermatogonium is disrupted by rotating-knife type crusher or sonicator.

6. The process according to claim 1, further comprising a step for hydrolysis of RNA.

7. The process according to claim 6, wherein said step for hydrolysis of RNA is performed by the alkali or RNase.

8. A process for obtaining deoxyribonucleic acid (DNA) from fish spermatogonium, which comprises:
    i) disrupting a fish spermatogoniurn in an alkaline solution of pH 8 to pH 12 that contains not less than 4 M of salts selected from the group consisting essentially of sodium nitrite, sodium carbonite, and sodium phosphate;
    ii) effectuating acylation reaction of a mixture obtained in step i); and
    iii) adding ethanol solution to the mixture obtained in step ii) to precipitate DNA.

9. The process according to claim 8, wherein said acylation reaction is performed by using anhydride compounds.

10. The process according to claim 9, wherein said anhydride compound is acetic anhydride.

* * * * *

UNITED STATES PATENT AND TRADEMARK OFFICE
CERTIFICATE OF CORRECTION

PATENT NO. : 6,759,532 B2
DATED : July 6, 2004
INVENTOR(S) : Park et al.

It is certified that error appears in the above-identified patent and that said Letters Patent is hereby corrected as shown below:

Column 8,
Line 5, after "from fish" and before "which comprises:" please replace "spermatogoflium," with -- spermatogonium, --.
Line 6, after "disrupting a fish" and before "to produce a", please replace "spermatogofliulfi" with -- spermatogonium --.
Line 15, after "to a mixture obtained" and before "step", please replace "iii" with -- in --.
Line 20, after "according to claim" and before "wherein said", please insert -- 1, --.
Line 22, after "according to claim" and before "wherein said", please replace "1," with -- 3, --.

Signed and Sealed this

Eighth Day of February, 2005

JON W. DUDAS
*Director of the United States Patent and Trademark Office*